US008546537B2

(12) United States Patent
Kodama et al.

(10) Patent No.: US 8,546,537 B2
(45) Date of Patent: Oct. 1, 2013

(54) STREPTAVIDIN HAVING LOW IMMUNOGENICITY AND USE THEREOF

(75) Inventors: Tatsuhiko Kodama, Tokyo (JP); Takao Hamakubo, Tokyo (JP); Hirofumi Doi, Tokyo (JP); Akira Sugiyama, Tokyo (JP); Kouhei Tsumoto, Tokyo (JP)

(73) Assignees: The University of Tokyo, Tokyo (JP); Perseus Proteomics Inc., Tokyo (JP)

( * ) Notice: Subject to any disclaimer, the term of this patent is extended or adjusted under 35 U.S.C. 154(b) by 65 days.

(21) Appl. No.: 13/202,102

(22) PCT Filed: Feb. 19, 2010

(86) PCT No.: PCT/JP2010/001100

§ 371 (c)(1), (2), (4) Date: Oct. 31, 2011

(87) PCT Pub. No.: WO2010/095455

PCT Pub. Date: Aug. 26, 2010

(65) Prior Publication Data

US 2012/0039879 A1 Feb. 16, 2012

(30) Foreign Application Priority Data

Feb. 20, 2009 (JP) ................................ 2009-037750

(51) Int. Cl.
*C07K 14/00* (2006.01)
*C07H 21/02* (2006.01)

(52) U.S. Cl.
USPC .......................................... 530/350; 536/23.1

(58) Field of Classification Search
USPC ........................................ 530/350; 536/23.1
See application file for complete search history.

(56) References Cited

U.S. PATENT DOCUMENTS

| | | | |
|---|---|---|---|
| 5,608,060 | A | 3/1997 | Axworthy et al. |
| 5,672,691 | A | 9/1997 | Kopetzki et al. |
| 6,022,951 | A | 2/2000 | Sano et al. |
| 2003/0143233 | A1 | 7/2003 | Goshorn et al. |

FOREIGN PATENT DOCUMENTS

| | | |
|---|---|---|
| JP | 2003-501096 | 1/2003 |
| WO | WO 00/75333 | 12/2000 |

OTHER PUBLICATIONS

Meyer, D.L. et al., "Reduced antibody response to streptavidin through site-directed mutagenesis", Protein Science, 10:491-503, 2001.
Schultz, J. et al., "A tetravalent single-chain antibody-streptavidin fusion protein for pretargeted lymphoma therapy", Cancer Research 60:6663-6669, 2000.
Subramanian, N. et al., "Mapping the common antigenic determinants in avidin and streptavidin", Biochemistry and Molecular Biology International, 43(2):375-382, 1997.
International Preliminary Report on Patentability; PCT/JP2010/001100; issued Sep. 22, 2011 (Japanese and English language versions).
Canadian Office Action issued with respect to patent family member Canadian Patent App. No. 2,753,048, dated Apr. 12, 2013.
Japanese Office Action issued with respect to patent family member Japanese Patent App. No. 2011-500525, mailed May 21, 2013, along with an English language excerption.
Extended European Search Report issued with respect to patent family member European Patent App. No. 10743584.4, dated Jun. 5, 2013.
Watanabe et al., "Four-Base Codon-Mediated Saturation Mutagenesis in a Cell-Free Translation System", Journal of Bioscience and Bioengineering, vol. 105, No. 3, pp. 211-215, 2008.

*Primary Examiner* — Karen Cochrane Carlson

(74) *Attorney, Agent, or Firm* — Greenblum & Bernstein, P.L.C.

(57) ABSTRACT

It is an object of the present invention to provide a mutant streptavidin wherein the immunogenicity (antigenicity) in mammals of a streptavidin is reduced. The present invention provides a mutant streptavidin, which comprises an amino acid sequence in which (a) the arginine residue at position 72 is substituted with another amino acid residue, and (b) any one or more of the tyrosine residue at position 10, the tyrosine residue at position 71, the glutamic acid residue at position 89, the arginine residue at position 91, and the glutamic acid residue at position 104 are substituted with other amino acid residues, with respect to the amino acid sequence of a core streptavidin as shown in SEQ ID NO: 2, and which has decreased immunogenicity as compared with that of a wild-type streptavidin.

10 Claims, 8 Drawing Sheets

STREPTAVIDIN HAVING LOW IMMUNOGENICITY AND USE THEREOF

SEQUENCE LISTING

The instant application contains a Sequence Listing which has been submitted in ASCII format via EFS-Web and is hereby incorporated by reference in its entirety. Said ASCII copy, created on Oct. 31, 2011, is named P40631.txt and is 15,503 bytes in size.

TECHNICAL FIELD

The present invention relates to a mutant streptavidin whose immunogenicity has been decreased, and the use thereof. More specifically, the present invention relates to a mutant streptavidin whose immunogenicity has been decreased by introducing mutations into amino acids, and the use thereof.

BACKGROUND ART

Avidin and biotin, or streptavidin and biotin have an extremely high affinity (Kd=$10^{-15}$ to $10^{-14}$ M). This is one of the strongest interactions between two biomolecules. At present, the interaction between avidin/streptavidin and biotin has been widely applied in the field of biochemistry, molecular biology or medicine (Green, (1975), Adv. Protein Chem., 29: 85-133; Green, (1990), Methods Enzymol., 184: 51-67). Avidin is a basic glycoprotein derived from albumen, and its isoelectric point exceeds 10. On the other hand, streptavidin is a protein derived from one type of *Streptomyces* (*Streptomyces avidinii*). Its isoelectric point is around the neutral range, and it does not comprise a sugar chain. The two types of proteins each form a tetramer, and they each bind to a molecule of biotin per subunit. Their molecular weight is approximately 60 kDa.

In recent years, a drug delivery method involving the combination of an antibody molecule with the aforementioned high binding ability of such avidin/streptavidin and biotin, namely, a pretargeting method has been conceived (Hnatowich, (1987), J. Nucl. Med., 28, 1294-1302). However, since a chicken-derived avidin or a microorganism-derived streptavidin exhibits high immunogenicity in human bodies, it has been problematic in that an anti-avidin/streptavidin antibody is generated at an early stage after administration of such avidin/streptavidin to a human body. This is a cause that prevents the practical use of a pretargeting method (Paganelli, (1991), Cancer Res., 51, 5960-5966).

In order to solve the aforementioned problem, a study paper regarding reduction in the immunogenicity of a streptavidin had been published in years past (Subramanian, (1998), Bioch. and Mol. biol. Int., 43, 357-82). However, the problem regarding the immunogenicity of a streptavidin in human bodies has not yet been solved.

PRIOR ART DOCUMENTS

Patent Documents

Patent Document 1: U.S. Pat. No. 5,672,691

Patent Document 2: U.S. Pat. No. 6,022,951

Non-Patent Documents

Non-Patent Document 1: Green, (1975), Adv. Protein Chem., 29: 85-133;

Non-Patent Document 2: Green, (1990), Methods Enzymol., 184: 51-67

Non-Patent Document 3: Hnatowich, (1987), J. Nucl. Med., 28, 1294-1302

Non-Patent Document 4: Paganelli, (1991), Cancer Res., 51, 5960-5966

Non-Patent Document 5: Mapping the common antigenic determinants in avidin and streptavidin. Subramanian, N et al. Biochemistry and Molecular biology International. 1997, 43, 357-82

Non-Patent Document 6: Reduced antibody response to streptavidin through site-directed mutagenesis, Meyer, D L et al. Protein Science., 2001, 10, 491-503

Non-Patent Document 7: Biotin Reagents for Antibody Pretargeting. 4., Wilbur D S et al. Bioconjugate Chemistry., 2000, 11(4), 569-583

SUMMARY OF INVENTION

Object to be Solved by the Invention

It is an object of the present invention to provide a mutant streptavidin (a streptavidin with low immunogenicity), which is produced by reducing the immunogenicity (antigenicity) in mammals of a streptavidin that is a protein derived from *Streptomyces avidinii* belonging to microorganisms, wherein the mutant streptavidin suppresses the generation of an anti-streptavidin antibody in animal bodies and maintains the binding ability of a streptavidin to a biotin, and it can be used for various purposes in the medical and other industries. It is another object of the present invention to provide a diagnostic or therapeutic agent in which the above-described mutant streptavidin is used, and a diagnostic or therapeutic kit in which the above-described mutant streptavidin is used.

Means for Solving the Object

The present inventor has conducted intensive studies directed towards achieving the aforementioned objects. The inventor selected amino acids that act as antigenic sites in human bodies on the basis of the three-dimensional structure of a streptavidin and the analysis of the frequency of appearance of pentapeptides, and as a result, the inventor selected amino acid candidates for the reduction of immunogenicity. Subsequently, a point mutation was introduced into a gene sequence using a wild-type streptavidin as a template, so as to convert amino acids to amino acid candidates having low immunogenicity. Thereafter, protein expression was carried out, and protein purification was then carried out. Moreover, a crab-eating monkey was immunized with a wild-type streptavidin, and the thus prepared anti-streptavidin antiserum was then used in the analysis of reactivity with these mutant streptavidins. As a result, the present inventor identified a mutant streptavidin whose reactivity with the antiserum was decreased by approximately 40% or more, as compared with the wild-type streptavidin, thereby completing the present invention.

Thus, the following invention is provided according to the present invention.

(1) A mutant streptavidin, which comprises an amino acid sequence in which (a) the arginine residue at position 72 is substituted with another amino acid residue, and (b) any one or more of the tyrosine residue at position 10, the tyrosine residue at position 71, the glutamic acid residue at position 89, the arginine residue at position 91, and the glutamic acid residue at position 104 are substituted with other amino acid residues, with respect to the amino acid sequence of a core streptavidin as shown in SEQ ID NO: 2, and which has decreased immunogenicity as compared with that of a wild-type streptavidin.

(2) The mutant streptavidin according to (1), which comprises an amino acid sequence in which (a) the tyrosine residue at position 71 and the arginine residue at position 72 are substituted with other amino acid residues, and (b) any one or more of the tyrosine residue at position 10, the glutamic acid residue at position 89, the arginine residue at position 91, and the glutamic acid residue at position 104 are substituted with other amino acid residues, with respect to the amino acid sequence of a core streptavidin as shown in SEQ ID NO: 2.

(3) The mutant streptavidin according to (1) or (2), which has any one or more mutations as described below with respect to the amino acid sequence of a core streptavidin as shown in SEQ ID NO: 2:

(1) a mutation in which the tyrosine residue at position 10 is substituted with serine or threonine;

(2) a mutation in which the tyrosine residue at position 71 is substituted with alanine or serine;

(3) a mutation in which the arginine residue at position 72 is substituted with lysine;

(4) a mutation in which the glutamic acid residue at position 89 is substituted with aspartic acid;

(5) a mutation in which the arginine residue at position 91 is substituted with lysine; and (6) a mutation in which the glutamic acid residue at position 104 is substituted with glutamine or asparagine.

(4) A mutant streptavidin, which comprises an amino acid sequence having any one or more mutations as described below with respect to the amino acid sequence of a core streptavidin as shown in SEQ ID NO: 2, and which has decreased immunogenicity as compared with that of a wild-type streptavidin:

(1) a mutation in which the tyrosine residue at position 10 is substituted with serine or threonine;

(2) a mutation in which the tyrosine residue at position 71 is substituted with alanine or serine;

(3) a mutation in which the arginine residue at position 72 is substituted with lysine;

(4) a mutation in which the glutamic acid residue at position 89 is substituted with aspartic acid;

(5) a mutation in which the arginine residue at position 91 is substituted with lysine; and (6) a mutation in which the glutamic acid residue at position 104 is substituted with glutamine or asparagine.

(5) A mutant streptavidin, which comprises an amino acid sequence having the mutations as described below with respect to the amino acid sequence of a core streptavidin as shown in SEQ ID NO: 2, and which has decreased immunogenicity as compared with that of a wild-type streptavidin:

(2) a mutation in which the tyrosine residue at position 71 is substituted with alanine or serine;

(3) a mutation in which the arginine residue at position 72 is substituted with lysine;

(4) a mutation in which the glutamic acid residue at position 89 is substituted with aspartic acid; and (6) a mutation in which the glutamic acid residue at position 104 is substituted with glutamine or asparagine.

(6) The mutant streptavidin according to (5), which further comprises the following mutations:

(1) a mutation in which the tyrosine residue at position 10 is substituted with serine or threonine; and (5) a mutation in which the arginine residue at position 91 is substituted with lysine.

(7) A mutant streptavidin, which comprises an amino acid sequence having all of the following mutations with respect to the amino acid sequence of a core streptavidin as shown in SEQ ID NO: 2:

(1) a mutation in which the tyrosine residue at position 10 is substituted with serine;

(2) a mutation in which the tyrosine residue at position 71 is substituted with serine;

(3) a mutation in which the arginine residue at position 72 is substituted with lysine;

(4) a mutation in which the glutamic acid residue at position 89 is substituted with aspartic acid;

(5) a mutation in which the arginine residue at position 91 is substituted with lysine; and (6) a mutation in which the glutamic acid residue at position 104 is substituted with glutamine or asparagine.

(8) DNA which encodes the mutant streptavidin according to any one of (1) to (7).

(9) A conjugate of mutant streptavidin and antibody, which is obtained by allowing an antibody to bind to the mutant streptavidin according to any one of (1) to (7).

(10) A therapeutic or diagnostic agent which comprises the conjugate of mutant streptavidin and antibody according to (9).

(11) A therapeutic or diagnostic kit, which comprises: (a) the conjugate of mutant streptavidin and antibody according to (9); and (b) a diagnostic or therapeutic agent labeled with biotin having an affinity for streptavidin or a derivative thereof.

Advantageous Effects of Invention

The mutant streptavidin of the present invention is characterized in that it has decreased immunogenicity (antigenicity) in mammals, while maintaining its binding ability to a biotin. Thus, the generation of an anti-streptavidin antibody is suppressed in animal bodies. The mutant streptavidin of the present invention can be used for various purposes in the medical and other industries.

DESCRIPTION OF EMBODIMENTS

Figure 1:
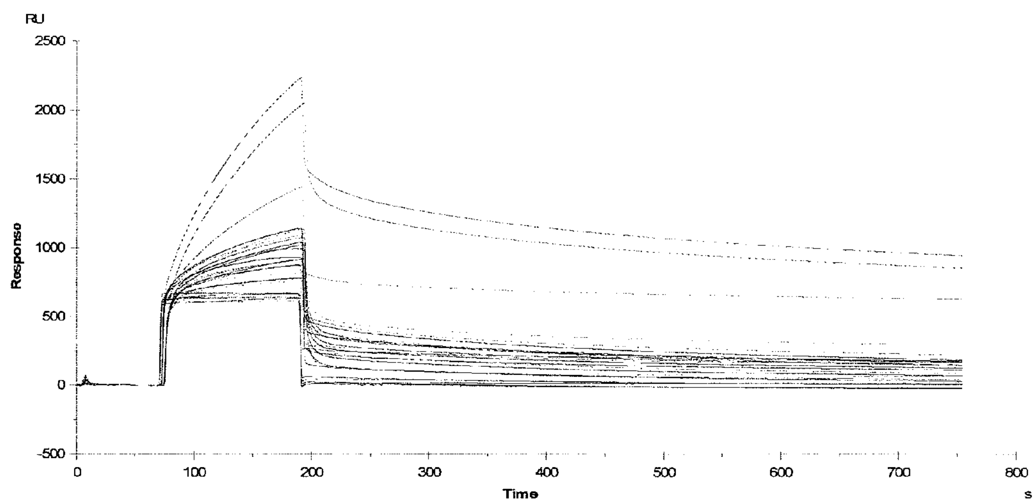
FIG. 1 shows a sensorgram in the Biacore analysis.

Hereinafter, the present invention will be described more in detail.

The mutant streptavidin of the present invention is characterized in that it has a certain amino acid mutation with respect to the amino acid sequence of a core streptavidin as shown in SEQ ID NO: 2 and has decreased immunogenicity as compared with that of a wild-type streptavidin.

The amino acid sequence of a wild-type (native) core streptavidin is shown in SEQ ID NO: 2 in the sequence listing, and a nucleotide sequence encoding the aforementioned amino acid sequence is shown in SEQ ID NO: 1 in the sequence listing.

According to a first aspect, the mutant streptavidin of the present invention comprises an amino acid sequence in which (a) the arginine residue at position 72 is substituted with another amino acid residue, and (b) any one or more of the tyrosine residue at position 10, the tyrosine residue at position 71, the glutamic acid residue at position 89, the arginine residue at position 91, and the glutamic acid residue at position 104 are substituted with other amino acid residues, with respect to the amino acid sequence of a core streptavidin as shown in SEQ ID NO: 2.

According to a second aspect, the mutant streptavidin of the present invention comprises an amino acid sequence having any one or more mutations as described below with respect to the amino acid sequence of a core streptavidin as shown in SEQ ID NO: 2:

(1) a mutation in which the tyrosine residue at position 10 is substituted with serine or threonine;

(2) a mutation in which the tyrosine residue at position 71 is substituted with alanine or serine;

(3) a mutation in which the arginine residue at position 72 is substituted with lysine;

(4) a mutation in which the glutamic acid residue at position 89 is substituted with aspartic acid;

(5) a mutation in which the arginine residue at position 91 is substituted with lysine; and (6) a mutation in which the glutamic acid residue at position 104 is substituted with glutamine or asparagine.

When the tyrosine residue at position 10 is substituted with another amino acid residue, specific examples of such another amino acid residue include glycine, serine and threonine. Of these, serine or threonine is particularly preferable.

When the tyrosine residue at position 71 is substituted with another amino acid residue, specific examples of such another amino acid residue include glycine, alanine and serine. Of these, alanine or serine is particularly preferable.

When the arginine residue at position 72 is substituted with another amino acid residue, specific examples of such another amino acid residue include glycine and lysine. Of these, lysine is particularly preferable.

When the glutamic acid residue at position 89 is substituted with another amino acid residue, specific examples of such another amino acid residue include glycine, alanine and aspartic acid. Of these, aspartic acid is particularly preferable.

When the arginine residue at position 91 is substituted with another amino acid residue, specific examples of such another amino acid residue include glycine and lysine. Of these, lysine is particularly preferable.

When the glutamic acid residue at position 104 is substituted with another amino acid residue, specific examples of such another amino acid residue include serine, glutamine and asparagine. Of these, glutamine or asparagine is particularly preferable.

The expression " . . . having decreased immunogenicity as compared with that of a wild-type streptavidin" is used in the present invention to mean that, when a mutant streptavidin is administered to a mammal such as a human, the immunogenicity of the mutant streptavidin is reduced. A decrease of the immunogenicity can be confirmed by the following method, for example. That is to say, the reactivity of the mutant streptavidin of the present invention with anti-streptavidin antiserum, which has been obtained by immunizing a crab-eating monkey with a wild-type streptavidin, is analyzed. If the reactivity of the mutant streptavidin with the aforementioned anti-streptavidin antiserum is decreased as compared with that of the wild-type streptavidin, it can be determined that the immunogenicity of the mutant streptavidin is decreased as compared with that of the wild-type streptavidin. When a decrease of the immunogenicity is determined by the above-described method, the immunogenicity of the mutant streptavidin of the present invention is decreased by preferably 80% or less, more preferably 60% or less, further preferably 20% or less, still further preferably 15% or less, still further preferably 10% or less, and particularly preferably 5% or less, as compared with the immunogenicity of the wild-type streptavidin.

According to the present invention, there is further provided DNA which encodes the above-described mutant streptavidin of the present invention. The DNA of the present invention can be produced by performing site-directed mutagenesis on DNA encoding a wild-type (native) streptavidin.

The above-described DNA which encodes the mutant streptavidin of the present invention can be incorporated into a vector, and it can be then used. In particular, in order to produce the mutant streptavidin of the present invention, DNA which encodes the mutant streptavidin of the present invention is incorporated into an expression vector, and a host is then transformed with this expression vector, so that the mutant streptavidin of the present invention can be expressed therein.

When *Escherichia coli* is used as a host, the vector used in the present invention preferably has a replication origin (ori) and also has a gene for selecting the transformed host (e.g. a drug-resistance gene that is resistant to drugs, such as ampicillin, tetracycline, kanamycin or chloramphenicol, etc.). Moreover, an expression vector preferably has a promoter capable of efficiently expressing the mutant streptavidin of the present invention in a host, such as a lacZ promoter or a T7 promoter. Examples of such a vector include an M13 vector, a pUC vector, pBR322, pBluescript, pCR-Script, pGEX-5X-1 (Pharmacia), "QIAexpress system" (QIAGEN), pEGFP, and pET (in this case, BL21 that expresses T7 RNA polymerase is preferably used as a host). Furthermore, a signal sequence and the like may be added to such a vector, so as to increase the yield of the mutant streptavidin of the present invention.

A vector can be introduced into a host cell by applying a calcium chloride method or an electroporation method, for example. Further, a sequence that encodes a tag for improving solubility, such as glutathione S-transferase, thioredoxin or a maltose-binding protein, may be added. Still further, a sequence that encodes a tag designed for facilitating purification, such as a polyhistidine tag, a Myc epitope, a hemagglutinin (HA) epitope, a T7 epitope, an Xpress tag, a FLAG tag or other known tag sequences, may also be added.

Other than *Escherichia coli*, examples of an expression vector include: mammal-derived expression vectors (for example, pcDNA3 (manufactured by Invitrogen), pEGF-BOS (Nucleic Acids. Res. 1990, 18(17), p. 5322), pEF and pCDM8); insect cell-derived expression vectors (for example, "Bac-to-BAC baculovirus expression system" (manufactured by Gibco-BRL) and pBacPAK8); plant-derived expression vectors (for example, pMH1 and pMH2); animal virus-derived expression vectors (for example, pHSV, pMV and pAdexLcw); retrovirus-derived expression vectors (for example, pZIPneo); yeast-derived expression vectors (for example, "*Pichia* Expression Kit" (manufactured by Invitrogen), pNV11 and SP-Q01); *Bacillus subtilis*-derived expression vectors (for example, pPL608 and pKTH50).

When the expression of the present mutant streptavidin in an animal cell such as a CHO cell, a COS cell or an NIH3T3 cell is intended, it is essential for the expression vector to have a promoter necessary for the expression of the mutant streptavidin in such an animal cell, such as an SV40 promoter (Mulligan et al., Nature (1979) 277, 108), an MMLV-LTR promoter, an EF1α promoter (Mizushima et al., Nucleic Acids Res. (1990) 18, 5322) or a CMV promoter. It is more preferable if the expression vector has a gene for selecting the transformation of a cell (for example, a drug-resistance gene capable of determining transformation with the use of drugs (neomycin, G418, etc.)). Examples of a vector having such properties include pMAM, pDR2, pBK-RSV, pBK-CMV, pOPRSV and pOP13.

The type of a host cell, into which a vector is introduced, is not particularly limited. Either prokaryotes or eukaryotes may be used. It is possible to use *Escherichia coli* or various types of animal cells, for example.

In the case of using a eukaryotic cell, for example, an animal cell, a plant cell or a fungal cell can be used as a host. Examples of an animal cell that can be used herein include: mammalian cells such as a CHO cell, a COS cell, a 3T3 cell, a HeLa cell or a Vero cell; and insect cells such as Sf9, Sf21 or Tn5. When the expression of a large amount of the mutant streptavidin in an animal cell is intended, a CHO cell is particularly preferable. A vector can be introduced into a host cell by a calcium phosphate method, a DEAE-dextran method, a method using cationic ribosome DOTAP (manufactured by Boehringer Mannheim), an electroporation method, a lipofection method or the like.

As a plant cell, a cell from *Nicotiana tabacum* has been known as a protein-producing system, for example. These cells may be subjected to callus culture. Examples of a known fungal cell include: yeast cells including genus *Saccharomyces* such as *Saccharomyces cerevisiae*; and filamentous fungi including genus *Aspergillus* such as *Aspergillus niger.*

Examples of a procaryotic cell that can be used herein include *Escherichia coli* (*E. coli*), such as JM109, DH5α or HB101. Moreover, *Bacillus subtilis* has been known.

These cells are transformed with the DNA of the present invention, and the transformed cells are then cultured in vitro, so as to obtain the mutant streptavidin of the present invention. The culture can be carried out in accordance with a known culture method. Examples of a culture solution of animal cells that can be used herein include DMEM, MEM, RPMI1640, and IMDM. During the culture, a serum infusion such as fetal calf serum (FCS) may be used in combination, or serum free culture may also be carried out. The pH applied during the culture is preferably approximately pH 6 to 8. The culture is generally carried out at a temperature of approximately 30° C. to 40° C. for approximately 15 to 200 hours. As necessary, medium replacement, ventilation and stirring are carried out. Furthermore, growth factors may also be added to promote the growth of cells.

Moreover, according to the present invention, there are provided: a conjugate of mutant streptavidin and antibody, which is obtained by binding an antibody to the mutant streptavidin of the present invention; and a therapeutic or diagnostic agent which comprises the conjugate of mutant streptavidin and antibody. Furthermore, the above-described conjugate of mutant streptavidin and antibody is combined with a diagnostic or therapeutic substance that has been labeled with a biotin having an affinity for streptavidin or a derivative thereof, so that it can be provided as a therapeutic or diagnostic kit.

Specifically, in the present invention, a fused body of a cancer antigen-specific antibody molecule and the mutant streptavidin of the present invention is prepared, and the prepared fused body is then administered to a patient, so that the mutant streptavidin of the present invention can be accumulated in a cancer cell-specific manner. Subsequently, a diagnostic or therapeutic substance (a radioisotope, a low-molecular-weight compound, a protein, etc.) bound to a biotin having an affinity for a streptavidin or a derivative thereof is administered to a patient, so that the substance can be accumulated exactly in cancer cells. In the present invention, the generation of an antibody is suppressed by a reduction in immunogenicity, and thereby, clearance of the mutant streptavidin from the body in an early stage caused by the antibody, or shock such as anaphylaxis, can be prevented.

Various types of molecules can be used as antibodies which are to be bound to the mutant streptavidin. Either a polyclonal antibody or a monoclonal antibody may be used. The subclass of the antibody is not particularly limited. Preferably, IgG and particularly preferably, $IgG_1$ is used. Furthermore, the term "antibody" includes all of modified antibodies and antibody fragments. Examples of such an antibody include: a humanized antibody; a human type antibody; a human antibody; antibodies from various types of animals such as a mouse, a rabbit, a rat, a guinea pig and a monkey; a chimeric antibody between a human antibody and an antibody from a different type of animal; diabody; scFv; Fd; Fab; Fab'; and $F(ab)'_2$. However, examples are not limited thereto.

A conjugate of the mutant streptavidin and an antibody can be obtained by applying a method known to persons skilled in the art. For example, the conjugate can be obtained by a chemical bond method (U.S. Pat. No. 5,608,060). Alternatively, DNA encoding the mutant streptavidin is ligated to DNA encoding an antibody, and using an expression vector or the like, the ligated DNA is then expressed in a host cell, so that the conjugate can be obtained in the form of a fusion protein. The DNA encoding the mutant streptavidin may be ligated to the DNA encoding an antibody via DNA encoding a suitable peptide, called a linker. The conjugate of mutant streptavidin and antibody is desirably produced, while keeping the specific binding ability between an antibody and a target molecule.

The present invention will be more specifically described in the following examples. However, these examples are not intended to limit the scope of the present invention.

EXAMPLES

Example 1

Designing of Streptavidin with Low Immunogenicity

Based on the nucleotide sequence of a core streptavidin and the amino acid sequence thereof, which are shown in SEQ ID NOS: 1 and 2, respectively, the sequences of mutant streptavidins having mutations that satisfy the below-mentioned conditions were examined, and mutant streptavidins having the mutations described in Table 1 were designed.

(1) A sequence, in which a fusion protein of a mutant streptavidin and an antibody is anticipated to reduce the immunogenicity in human bodies to the minimum.

(2) A sequence, which maintains as high an affinity for a biotin molecule as possible.

TABLE 1

| Mutation List | | | | | | |
|---|---|---|---|---|---|---|
| Name | Mutation 1 | Mutation 2 | Mutation 3 | Mutation 4 | Mutation 5 | Mutation 6 |
| mcSA010 | | Y83A | R84K | | | E116N |
| mcSA020 | | Y83A | R84K | | | E116Q |
| mcSA030 | | Y83S | R84K | | | E116N |
| mcSA040 | | Y83S | R84K | | | E116Q |
| mcSA114 | Y22S | Y83A | R84K | E101D | R103K | E116N |
| mcSA124 | Y22T | Y83A | R84K | E101D | R103K | E116N |
| mcSA214 | Y22S | Y83A | R84K | E101D | R103K | E116Q |
| mcSA224 | Y22T | Y83A | R84K | E101D | R103K | E116Q |
| mcSA314 | Y22S | Y83S | R84K | E101D | R103K | E116N |
| mcSA324 | Y22T | Y83S | R84K | E101D | R103K | E116N |
| mcSA414 | Y22S | Y83S | R84K | E101D | R103K | E116Q |
| mcSA424 | Y22T | Y83S | R84K | E101D | R103K | E116Q |
| mcSA001 | | | R84K | | | |
| mcSA002 | | Y83A | | | | E116N |
| mcSA003 | | Y83A | | | | E116Q |
| mcSA004 | | Y83S | | | | E116N |
| mcSA005 | | Y83S | | | | E116Q |
| mcSA083 | | | | | | E116N |
| mcSA091 | | | | | | E116Q |
| mcSA101 | | Y83A | R84K | | | |
| mcSA111 | | Y83S | R84K | | | |

Y22 in Table 1 corresponds to the tyrosine residue at position 10 in the amino acid sequence as shown in SEQ ID NO: 2 in the sequence listing. Y22S in Table 1 indicates the substitution of the tyrosine with serine, and Y22T in Table 1 indicates the substitution of the tyrosine with threonine.
Y83 in Table 1 corresponds to the tyrosine residue at position 71 in the amino acid sequence as shown in SEQ ID NO: 2 in the sequence listing. Y83A in Table 1 indicates the substitution of the tyrosine with alanine, and Y83S in Table 1 indicates the substitution of the tyrosine with serine.
R84 in Table 1 corresponds to the arginine residue at position 72 in the amino acid sequence as shown in SEQ ID NO: 2 in the sequence listing. R84K in Table 1 indicates the substitution of the arginine with lysine.
E101 in Table 1 corresponds to the glutamic acid residue at position 89 in the amino acid sequence as shown in SEQ ID NO: 2 in the sequence listing. E101D in Table 1 indicates the substitution of the glutamic acid with aspartic acid.
R103 in Table 1 corresponds to the arginine residue at position 91 in the amino acid sequence as shown in SEQ ID NO: 2 in the sequence listing. R103K in Table 1 indicates the substitution of the arginine with lysine.
E116 in Table 1 corresponds to the glutamic acid residue at position 104 in the amino acid sequence as shown in SEQ ID NO: 2 in the sequence listing. E116N in Table 1 indicates the substitution of the glutamic acid with asparagine, and E116Q in Table 1 indicates the substitution of the glutamic acid with glutamine.

Example 2

Production of Mutant Streptavidins (1) Synthesis of Nucleotide Sequence of Wild-Type Core Streptavidin The nucleotide sequence of a gene encoding a core streptavidin as shown in SEQ ID NO: 1 in the sequence listing was obtained using the service of artificial gene synthesis (Integrated DNA Technologies).

(2) Construction of Expression Vector

The above-obtained sequence was used as a template. Moreover, there were used the following Primers 1 and 2, which added a HindIII site onto the 5-terminal side and an EcoRI site onto the 3-terminal side by PCR. After completion of the PCR, the PCR product was treated with the restriction enzymes HindIII and EcoRI.

```
                                          (SEQ ID NO: 3)
Primer 1: GCTCTTCAAAGCTTTGGCCGAAGCTGGTATCACTG

                                          (SEQ ID NO: 4)
Primer 2: CTCGAGGAATTCTTAGCTAGCAGCAGAAGGCTTAAC
```

The thus restriction enzyme-treated sample was subjected to electrophoresis, and then to gel purification. Likewise, a pPAL7 vector (manufactured by BIO-RAD) was also treated with enzymes and was then subjected to gel purification. The purified vector was ligated to the purified PCR product according to a designated method using 2× Rapid Ligation Buffer and T4 DNA Polymerase (both of which were manufactured by Promega). *Escherichia coli* was transformed by adding 2 μl of the ligation product to 50 μl of DH5α competent cells (manufactured by TOYOBO). A plasmid was extracted using Miniprep Kit (manufactured by QIAGEN). The obtained plasmid was subjected to sequence analysis, so as to confirm its sequence.

(3) Production of Mutant Strains

Using the above-described wild-type streptavidin expression vector as a template, a codon sequence was altered by the substitution of the nucleotide sequence according to the Site-Directed Mutagenesis method, so as to convert the amino acid sequence to another amino acid sequence. Specifically, complementary primers each having 28 to 30 bases in length were designed, such that the nucleotide sequence to be altered could be positioned almost in the center. Using the wild-type streptavidin expression vector as a template, a PCR method was carried out. Thereafter, a template plasmid was cleaved with the restriction enzyme DpnI, so that the *Escherichia coli* was transformed. Primers:

```
                                          (SEQ ID NO: 5)
Y22S Fw: CACTGGCACCTGGTCGAACCAACTGGGGTC

                                          (SEQ ID NO: 6)
Y22T Fw: CACTGGCACCTGGACTAACCAACTGGGGTC

                                          (SEQ ID NO: 7)
E101D FW: CGTTGGCGGTGCTGATGCTCGTATCAACAC
```

-continued

```
                                        (SEQ ID NO: 8)
R103K FW: GGTGCTGATGCTAAGATCAACACTCAGTGG

                                        (SEQ ID NO: 9)
Y83A FW: GGAAAAACAACGCCCGTAATGCGCACAGCG

                                       (SEQ ID NO: 10)
Y83S FW: GGAAAAACAACTCGCGTAATGCGCACAGCG

                                       (SEQ ID NO: 11)
R84K FW: GAAAAACAACTATAAGAATGCGCACAGCG

                                       (SEQ ID NO: 12)
E116N FW: CATCCGGCACTACCAATGCGAATGCATGG

                                       (SEQ ID NO: 13)
E160Q FW: CATCCGGCACTACCCAAGCGAATGCATGG
```

(4) Expression of Recombinant Proteins

*Escherichia coli* BL21 (BIO-RAD) was transfected with a pPAL7 expression vector, into which the gene sequence of either a wild-type streptavidin or a mutant streptavidin had been incorporated, according to an ordinary method. The expression of each protein was carried out as follows. That is to say, the *Escherichia coli* was cultured at 37° C., until the cell density of the culture solution of *Escherichia coli* became 0.5 to 0.7 in OD (600 nm). Thereafter, IPTG (isopropyl-β-D-thiogalactopyranoside) was added to the culture solution to a final concentration of 1 mM. Protein expression was induced, and the culture was carried out at 20° C. for 24 hours. After completion of the culture for 24 hours, cells were collected by the centrifugation of the cell mass, and the collected cells were then preserved at −20° C. until protein purification.

(5) Purification of Recombinant Proteins

The recombinant protein was purified by a method using Profinity eXact Protein Purification System (manufactured by BIO-RAD). BugBuster (Novagen) was added in an amount of 1/20 of the culture volume to the cells, so that the cells were dissolved. After completion of centrifugation, the supernatant was defined as a total soluble protein. The recovered soluble fraction was treated in accordance with the direction for use of Profinity eXact Mini Spin Columns (BIO-RAD). A total soluble protein, a column-passed fraction, a washed fraction and an eluted fraction were subjected to SDS-PAGE electrophoresis using 10-20% Ready Gel J (manufactured by BIO-RAD). After completion of the electrophoresis, the protein was stained with SimplyBlue SafeStain (manufactured by Invitrogen), and the purity of the purified protein was confirmed.

Example 3

Production of Crab-Eating Monkey Anti-Streptavidin Antiserum

A recombinant streptavidin (manufactured by PIERCE) was administered at a dose of 1 mg per administration to a crab-eating monkey. The administration was carried out three times every two weeks. The day at which blood was collected before administration of the recombinant streptavidin was defined as Day 1. Then, blood was further collected on Days 8, 15, 29, 36, 50 and 57 (Ina Research Inc.).

Example 4

Analysis of Binding Ability of Protein to Biotin (1) Kinetics Analysis of Interaction Between Protein and Biotin Using Biacore Biosensor As a ligand (a substance to be attached to a sensor chip) used for a Biacore (registered trademark) biosensor, an anti-mouse IgG antibody (manufactured by GE Healthcare Biosciences) was used. On the other hand, as analytes (substances to be supplied to the flow channel system), a biotinylated mouse antibody and various types of mutant streptavidins were prepared, and intermolecular interaction was then analyzed using Biacore (registered trademark) 3000 (a biosensor based on the principle of surface plasmon resonance; manufactured by GE Healthcare Biosciences). The anti-mouse IgG antibody was immobilized on all of the flow cells of a CM5 sensor chip according to an amine coupling method. The amount of the antibody immobilized on each flow cell was 8000 RU. Subsequently, as references, non-biotinylated mouse antibodies were captured onto Flow Cells 1 and 3, and biotinylated mouse antibodies were captured onto Flow Cells 2 and 4. Various types of streptavidins were loaded in a running buffer (HBS-EP; manufactured by GE Healthcare Biosciences) on Flow Cells 1 and 2, or 3 and 4, at a flow rate of 20 μl/min for 2 minutes. Thereafter, dissociation of each sample was monitored for 7 minutes. Thereafter, a reproduction operation was carried out using a 10 mM glycine-HCl buffer (pH 1.7) (manufactured by GE Healthcare Biosciences), and repeat measurement was then carried out. Using the analysis software BIAevaluation ver. 4.1, a reaction kinetics analysis was performed on a 1:1 binding model based on the obtained sensorgram, so as to calculate an association rate constant ($k_a$) and a dissociation rate constant ($k_d$). A dissociation constant ($K_d$) was obtained from $k_d/k_a$.

The results of the kinetics analysis of the intermolecular interaction of a recombinant streptavidin and a biotin, which was carried out using Biacore (registered trademark) 3000 (a biosensor based on the principle of surface plasmon resonance; manufactured by GE Healthcare Biosciences), are as shown in Table 2.

TABLE 2

Kinetics of interaction between modified streptavidin and biotin

| Protein | Molecular mass (kDa) | Association rate constant $k_a$ ($M^{-1} S^{-1}$) | Dissociation rate constant $k_d$ ($S^{-1}$) | Dissociation constant $K_d$ (M) |
|---|---|---|---|---|
| cSA_WT | 60 | $2.81 \times 10^5$ | $6.32 \times 10^{-5}$ | $2.25 \times 10^{-10}$ |
| mcSA_W120A | 60 | $2.81 \times 10^5$ | $7.49 \times 10^{-4}$ | $3.53 \times 10^{-9}$ |
| mcSA10 | 60 | $2.81 \times 10^5$ | $8.96 \times 10^{-5}$ | $2.25 \times 10^{-10}$ |
| mcSA114 | 60 | $3.61 \times 10^5$ | $9.92 \times 10^{-5}$ | $2.74 \times 10^{-10}$ |
| mcSA124 | 60 | $3.06 \times 10^5$ | $5.38 \times 10^{-5}$ | $1.76 \times 10^{-10}$ |
| mcSA20 | 60 | $2.81 \times 10^5$ | $1.60 \times 10^{-4}$ | $4.27 \times 10^{-10}$ |
| mcSA214 | 60 | $2.64 \times 10^5$ | $1.21 \times 10^{-4}$ | $4.59 \times 10^{-10}$ |
| mcSA224 | 60 | $2.11 \times 10^5$ | $1.01 \times 10^{-4}$ | $4.81 \times 10^{-10}$ |
| mcSA30 | 60 | $2.81 \times 10^5$ | $1.55 \times 10^{-4}$ | $3.99 \times 10^{-10}$ |
| mcSA314 | 60 | $5.99 \times 10^5$ | $1.58 \times 10^{-4}$ | $2.64 \times 10^{-10}$ |
| mcSA324 | 60 | $3.26 \times 10^5$ | $7.18 \times 10^{-5}$ | $2.20 \times 10^{-10}$ |
| mcSA40 | 60 | $2.81 \times 10^5$ | $1.69 \times 10^{-4}$ | $2.57 \times 10^{-10}$ |
| mcSA414 | 60 | $2.31 \times 10^5$ | $5.18 \times 10^{-5}$ | $2.43 \times 10^{-10}$ |
| mcSA424 | 60 | $1.32 \times 10^5$ | $1.12 \times 10^{-4}$ | $8.45 \times 10^{-10}$ |

The dissociation constant of the modified streptavidin was of an order of magnitude of $10^{-10}$ M. This was the same order as that of the dissociation constant of a wild-type streptavidin, which we measured this time. From these results, it was revealed that the modified streptavidin was a protein having an extremely high affinity for a biotin, just as with the wild-type streptavidin. Thus, it is considered that the modified streptavidin can be applied to the streptavidin-biotin technique, which has been widely used at present.

(2) Analysis of Interaction Between Protein and Crab-Eating Monkey Antiserum Using Biacore Biosensor As ligands (substances to be attached to a sensor chip) used for a Biacore (registered trademark) biosensor, Amin-$PEG_3$-Biotin (Thermo SCIENTIFIC) and various types of modified streptavidins were used. On the other hand, as an analyte (a substance to be supplied to the flow channel system), there was prepared a crab-eating monkey antiserum that was 20-fold diluted with a running buffer (HBS-EP; manufactured by GE Healthcare Biosciences), and intermolecular interaction was then analyzed using Biacore (registered trademark) 3000 (a biosensor based on the principle of surface plasmon resonance; manufactured by GE Healthcare Biosciences). The Amin-$PEG_3$-Biotin (Thermo SCIENTIFIC) was immobilized on all of the flow cells of a CM5 sensor chip according to an amine coupling method. The amount of the Amin-$PEG_3$-Biotin immobilized on each flow cell was 160 RU on an average. Subsequently, a wild-type streptavidin was supplied to Flow Cell 2, and two different types of modified streptavidins were each supplied to Flow Cells 3 and 4, so that they were immobilized thereon by a binding reaction with a biotin. Flow Cell 1 was used as a reference.

Figure 2:
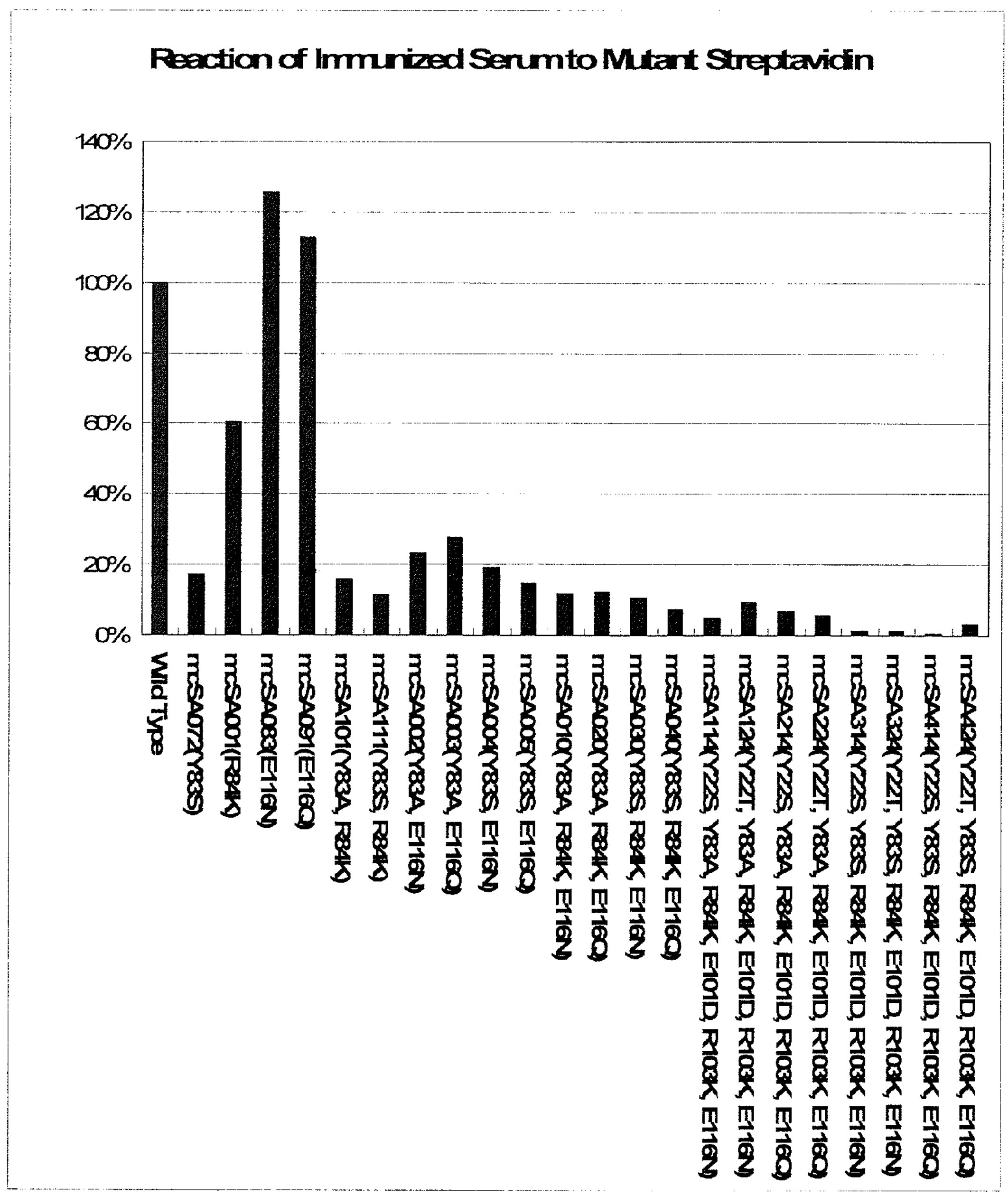
FIG. 2 shows the reactivity of antiserum with a mutant streptavidin.

The diluted crab-eating monkey antiserum was loaded in a running buffer (HBS-EP; manufactured by GE Healthcare Biosciences) at a measurement temperature of 37° C. at a flow rate of 5 μl/min for 2 minutes. Thereafter, dissociation of each sample was monitored for 7 minutes. Thereafter, a reproduction operation was carried out using a 10 mM glycine-HCl buffer (pH 1.7) (manufactured by GE Healthcare Biosciences), and repeat measurement was then carried out. Using the analysis software BIAevaluation ver. 4.1, the amount of a modified streptavidin bound and the reacting amount of an antiserum were obtained from the sensorgram (FIG. 1). The obtained values were standardized with the amount of a streptavidin bound to each flow cell, and the reactions of antiserums were compared. That is to say, numerical values were obtained using the formula: (value obtained after reaction of antiserum−value obtained before reaction of antiserum)/amount of streptavidin bound, and a graph was then made using the obtained values (FIG. 2).

Example 5

Analysis of Immunogenicity of Streptavidin in Silico

Utilizing Epibase T-cell epitope profiling service (Algonomics), a wild-type streptavidin, mcSA072, mcSA040, mcSA314 and mcSA414 were analyzed in terms of immunogenicity on an in silico basis (Desmet, (2005), Proteins, 58, 53-69; ES126528). As allotypes used in prediction, those having an appearance frequency of 30% or more in Caucasian, Oriental, Indo-European, Afro-American plus West African, Austronesian and Mestizo were selected. With regard to each allotype, a crystal structure, or a structure closest to such a crystal structure, which was modeled based on the crystal structure, was used, and a method involving an original method of disposing a side chain was applied (Desmet, (2002), Proteins, 48, 31-34). Subsequently, the free energy of binding of a receptor to a target peptide was calculated, and the strengths of antigenicities were classified based on the binding strength (Kapoerchan, (2009), Mol. Immunol. 47(5), 1091-1097).

A total of 78 types of HLA class II receptors, which included 37 types of DRB1, 8 types of DRB3/4/5, 23 types of DQ, and 10 types of DP, were subjected to profiling analysis regarding allotype level. The results are shown in Table 3 and Table 4. Table 3 shows a critical number of epitopes. This table demonstrated that the number of DBR1 epitopes was smallest and the number of DRB3/4/5 epitopes was largest in the wild-type streptavidin, and that, in mcSA314 and mcSA414, DP epitopes disappeared and the number of DQ epitopes was increased. Table 4 shows influential allotypes, and this table demonstrated that, in mcSA314 and mcSA414, the number of epitopes was decreased as compared with other proteins. From these results, the prediction results of immunogenicity were found to be the order of mcSA314<mcSA414<the wild-type streptavidin (wherein the leftmost mutant had the lowest immunogenicity).

TABLE 3

Results of T-Cell Epitope assay (Epibase) in silico

| | DRB1 | DRB3/4/5 | DQ | DP |
|---|---|---|---|---|
| Control Core Streptavidin | 45 | 12 | 4 | 1 |
| mcSA040 | 48 | 11 | 4 | 1 |
| mcSA072 | 47 | 11 | 4 | 1 |
| mcSA314 | 47 | 10 | 5 | 0 |
| mcSA414 | 46 | 10 | 5 | 0 |

TABLE 4

Results of T-Cell Epitope assay (Epibase) in silico

| Allele | Serotype | Frequency | Streptavidin critical binders | mcSA040 critical binders | mcSA072 critical binders | mcSA314 critical binders | mcSA414 critical binders |
|---|---|---|---|---|---|---|---|
| DPA1*0103/DPB1*0401 | DPw4 | 65% | 1 | 1 | 1 | 0 | 0 |
| DRB4*0101 | DR53 | 46% | 2 | 2 | 2 | 1 | 1 |
| DRB3*0202 | DR52 | 30% | 3 | 3 | 3 | 2 | 2 |
| DRB1*0701 | DR7 | 25% | 6 | 6 | 6 | 6 | 6 |
| DQA1*0501/DQB1*0201 | DQ2 | 25% | 0 | 0 | 0 | 1 | 1 |
| DPA1*0103/DPB1*0402 | DPw4 | 24% | 1 | 1 | 1 | 0 | 0 |
| DRB1*1501 | DR15(2) | 23% | 7 | 6 | 6 | 5 | 5 |
| DRB3*0101 | DR52 | 23% | 1 | 1 | 1 | 1 | 1 |
| DRB1*0301 | DR17(3) | 22% | 0 | 1 | 0 | 0 | 1 |
| DQA1*0501/DQB1*0301 | DQ7(3) | 21% | 1 | 1 | 1 | 1 | 1 |
| DPA1*0103/DPB1*0201 | DPw2 | 20% | 1 | 1 | 1 | 0 | 0 |
| DRB5*0101 | DR51 | 19% | 5 | 4 | 4 | 3 | 3 |
| DRB1*0101 | DR1 | 15% | 11 | 10 | 10 | 9 | 9 |
| DRB1*0401 | DR4 | 14% | 5 | 7 | 6 | 7 | 7 |

TABLE 4-continued

| Results of T-Cell Epitope assay (Epibase) in silico | | | | | | | |
|---|---|---|---|---|---|---|---|
| Allele | Serotype | Frequency | Streptavidin critical binders | mcSA040 critical binders | mcSA072 critical binders | mcSA314 critical binders | mcSA414 critical binders |
| DRB1*1101 | DR11(5) | 12% | 4 | 4 | 4 | 4 | 4 |
| DRB1*1301 | DR13(6) | 11% | 4 | 6 | 5 | 6 | 6 |
| DRB3*0201 | DR52 | 10% | 1 | 1 | 1 | 1 | 1 |

Example 6

Evaluation of Thermal Stability of Streptavidin Proteins

The following 5 types of proteins, a native streptavidin, mcSA040, mcSA072, mcSA314 and mcSA414, which had been purified in accordance with Example 2, were subjected to a thermal shift assay (Vedadi, (2006), Proc Natl Sci USA., 103(43), 15835-15840). Each sample was prepared in a real-time PCR tube (PCR Tube Strip, Flat Cap Strip; manufactured by BIO-RAD), so that the samples could have the following final concentrations. That is, SYPRO Orange was 5000-fold diluted, the concentration of each protein was set at 10 μM, and the buffer was set at 1×PBS. Moreover, for the purpose of accelerating the heat denaturation of each protein, the concentration of a guanidine-HCl solution was set at 0 M, 0.5 M, 1M and 2 M as a final concentration. The reaction volume was set at 20 μl. The CFX96 Real-Time PCR detection system (manufactured by BIO-RAD) was used as a measurement device. As a program mode of the CFX96 Real-Time PCR detection system, a program mode for use in FRET detection was used. The reaction and detection were carried out by a program for increasing the temperature by 0.5° C. every 10 seconds.

Figure 3:
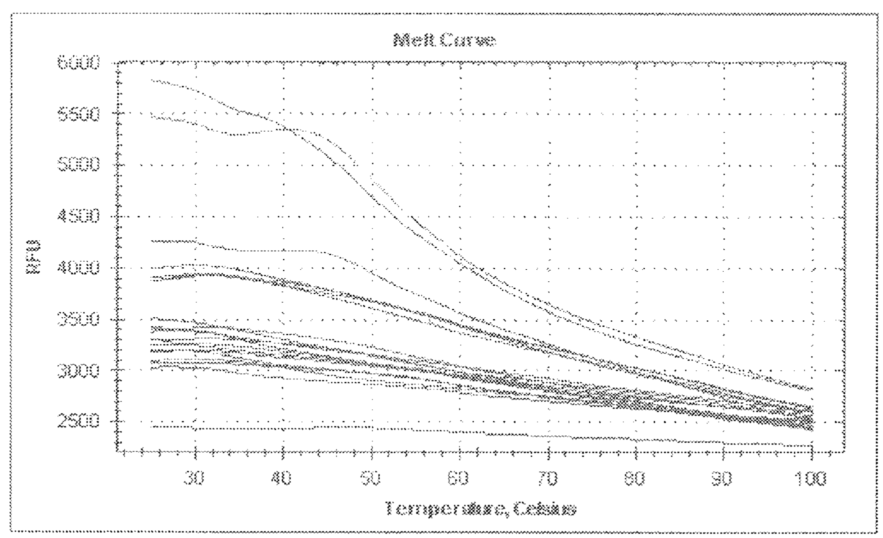
FIG. 3 shows the results of a thermal shift assay performed on a native streptavidin, mcSA040, mcSA072, mcSA314 and mcSA414.

The results of the thermal shift assay were analyzed. As a result, it was found that the modified streptavidins, namely, mcSA040, mcSA072, mcSA314 and mcSA414 exhibited thermal stability equivalent to that of the native streptavidin at 100° C. (FIG. 3). These results suggested that the above described mutation would reduce immunogenicity but would not affect thermal stability.

Example 7

Production of Modified Monoclonal Antibody (1) Preparation of Total RNA from Hybridoma Cell As a hybridoma that produces the monoclonal antibody B5209B (IgG2b), a hybridoma producing the monoclonal antibody B5209B described in JP Patent Publication (Kokai) No. 2008-290996 A was used. This hybridoma producing the monoclonal antibody B5209B was deposited with the International Patent Organism Depositary, the National Institute of Advanced Industrial Science and Technology, an Independent Administrative Institution under the Ministry of Economy, Trade and Industry (at the AIST Tsukuba Central 6, Higashi 1-1-1, Tsukuba, Ibaraki, Japan, (postal code: 305-8566)) under accession No. FERM P-21238 on Mar. 2, 2007. It was then transferred to an international deposition on Oct. 16, 2007, and received an accession No. FERM BP-10921.

The above-described monoclonal antibody B5209B (IgG2b)-producing hybridoma cells ($1\times10^7$ cells) were washed once with a phosphate buffered saline (PBS), and 1 mL of a Trizol solution (manufactured by Invitrogen) was added to the cell precipitate so as to solubilize it. The extract was passed through a 20-G injection needle twice to shear DNA. Thereafter, chloroform extraction, isopropanol precipitation and washing with 80% ethanol were carried out in accordance with an instruction manual included with the Trizol solution, thereby purifying total RNA. The total RNA was dissolved in diethyl pyrocarbonate-containing sterile distilled water. The obtained total RNA was subjected to agarose gel electrophoresis, so that it was confirmed not to be decomposed.

(2) Synthesis and Cloning of IgG Heavy Chain V Region (VH) cDNA

Using 5 μg of B5209B total RNA as a template, and also using, as a 3'-primer, a primer (5'-ccaagcttaggggccagtggatagactg-3') (SEQ ID NO: 14) based on the cDNA sequence of the 5'-terminus of a mouse IgG2 heavy chain C region, 1st strand cDNA was synthesized using SuperScript cDNA synthesis kit (manufactured by Invitrogen) in accordance with the instruction manual of the kit. The MuIgVH5'-A primer of the Mouse Ig-Primer Set manufactured by Novagen was added to the obtained 1st strand cDNA, and double-stranded cDNA was then amplified using the Expand High Fidelity PCR System (manufactured by Roche Diagnostics). The obtained double-stranded cDNA was subcloned into pGEM-T vector (manufactured by Promega) according to a TA cloning method, and it was then introduced into *Escherichia coli* DH5α, so as to obtain a plasmid-containing vector. With regard to 6 clones, their plasmid DNA was purified with Qiagen Plasmid Midi Kit (manufactured by QIAGEN), and the nucleotide sequence of the DNA was then determined according to an ordinary method. It was revealed that the amino acid sequence of the heavy chain variable region (VH) of the antibody was an amino acid sequence consisting of amino acids at positions 1 to 122 with respect to the amino acid sequence as shown in SEQ ID NO: 16.

(3) Determination of IgG Light Chain N-Terminal Amino Acid Sequence of Anti-ROBO1 Monoclonal Antibody B5209B Using a Protein G column (manufactured by GE Healthcare), an antibody was purified from a hybridoma serum-free culture supernatant that contained the monoclonal antibody B5209B (IgG2b) in accordance with the instruction manual included with the column.

The purified monoclonal antibody B5209B was subjected to electrophoresis using SDS-PAGE. The electrophoretic gel was transcribed to a PVDF membrane, and the PVDF membrane was then stained with Coomassie brilliant blue. The stained band of the IgG light chain was cut out, and the N-terminal amino acid sequence (DIQMT) was then determined by the Edman degradation method.

Figure 4:
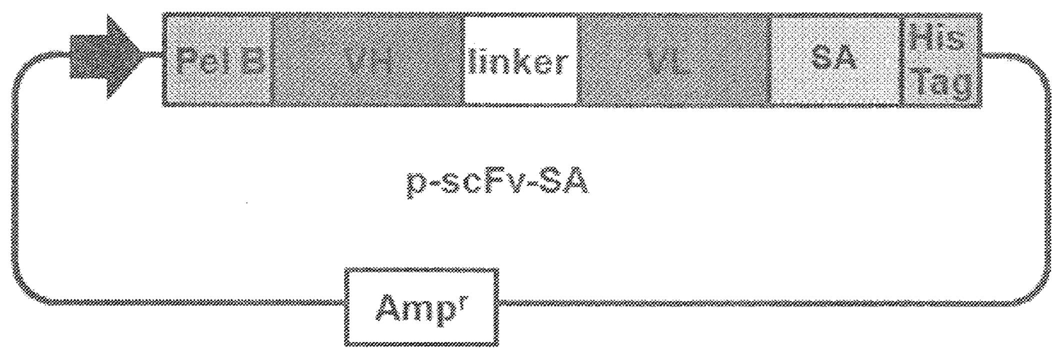
FIG. 4 shows the structure of an expression vector of B5209B mouse scFv-mcSA414 (SA).

(4) Construction of Expression Vector of B5209B Mouse-scFv-mcSA414 (FIG. 4)

An expression vector of B5209B mouse-scFv-mcSA414 having the structure shown in FIG. 4 was constructed. The nucleotide sequence of B5209B mouse-scFv-SA contained in the expression vector is as shown in SEQ ID NO: 15, and the amino acid sequence thereof is as shown in SEQ ID NO: 16. The amino acid sequence of the heavy chain variable region (VH) of the antibody corresponds to an amino acid sequence consisting of amino acids at positions 1 to 122 with respect to the amino acid sequence as shown in SEQ ID NO: 16. The amino acid sequence of the light chain variable region (VL) of the antibody corresponds to an amino acid sequence consisting of amino acids at positions 142 to 248 with respect to the amino acid sequence as shown in SEQ ID NO: 16.

(5) Method for Culturing B5209B Mouse-scFv-mcSA414

After transformation of *Escherichia coli* BL21 (DE3), it was cultured at 28° C. for approximately 20 hours in an LB plate medium containing 50 μg/ml ampicillin. Using an inoculating loop, a single colony was separated from the plate, and it was then inoculated into an LB test medium (3 mL) containing 50 μg/ml ampicillin. Thereafter, it was subjected to a shaking culture (at approximately 140 rpm) at 28° C. for approximately 18 hours. Subsequently, a total amount of preculture solution of 50 μg/ml ampicillin-containing 2×YT medium (1 L) was subcultured, and the resultant was then subjected to a shaking culture (at 125 rpm) at 28° C. IPTG having a final concentration of 0.5 mM was added to the culture at the time point of OD600=0.8, so as to induce expression. Thereafter, the culture was continuously carried out overnight (6) Method for Preparing B5209B Mouse-scFv-mcSA414

Figure 5:
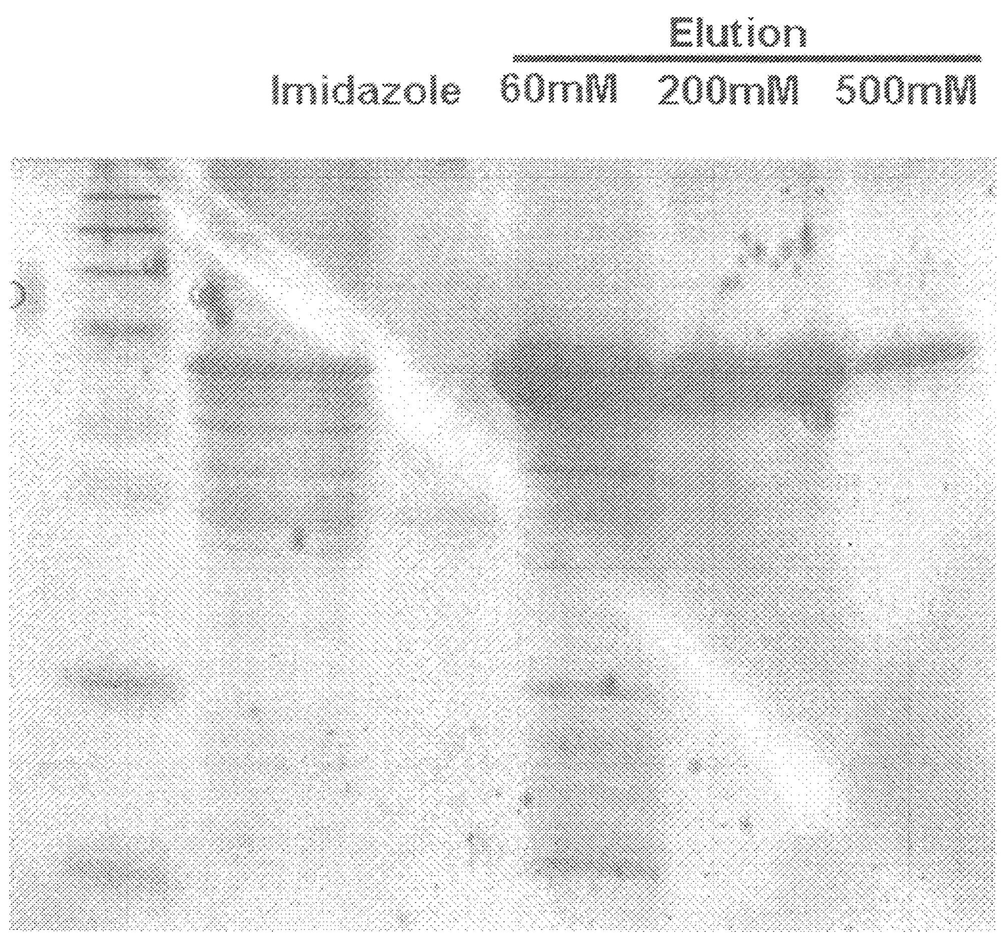
FIG. 5 shows the results obtained by purifying B5209B scFv-mcSA414 with a Ni2+ affinity column.
Figure 6:
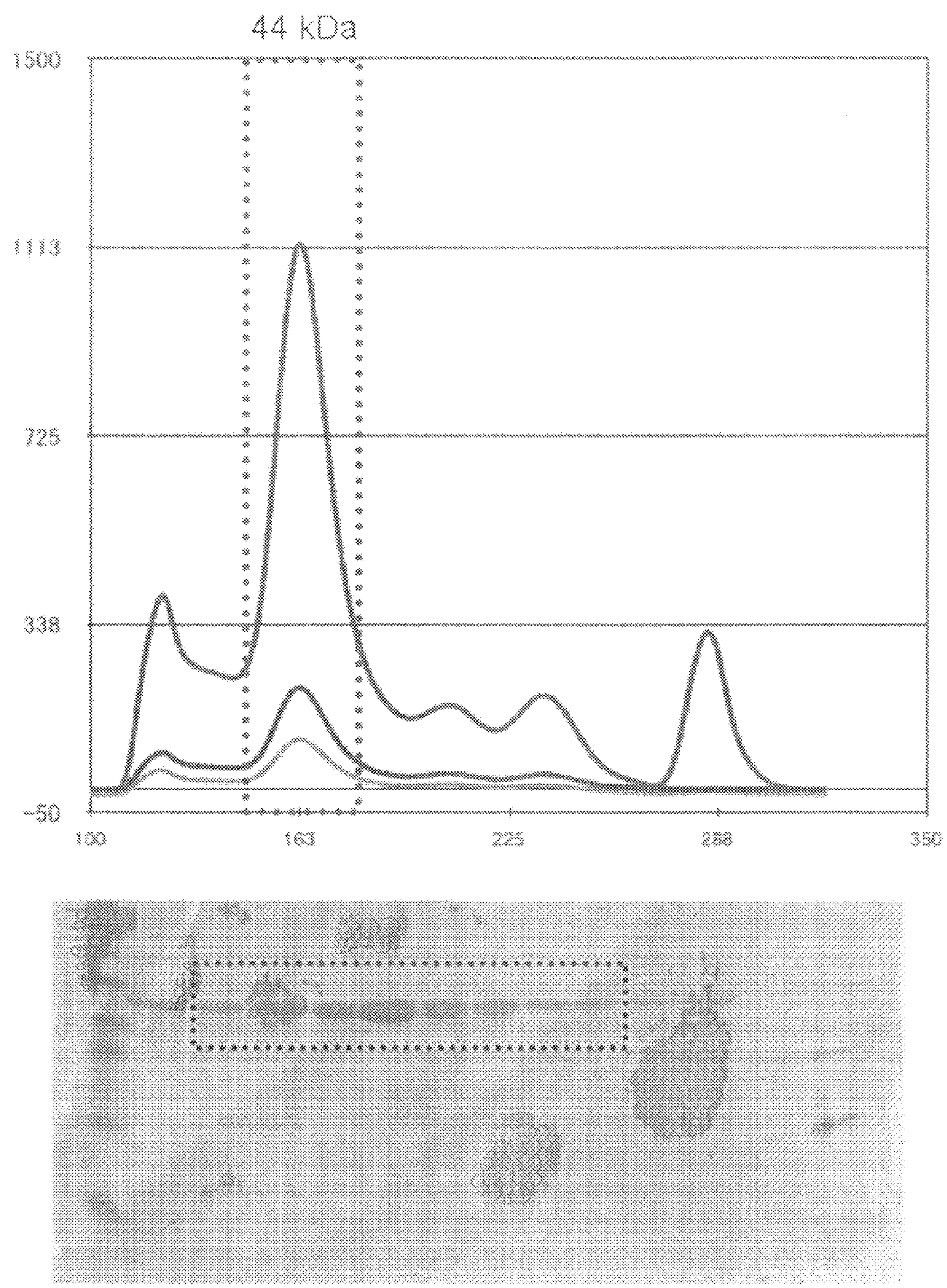
FIG. 6 shows the results obtained by finally purifying B5209B scFv-mcSA414 by size exclusion chromatography.

A protein of interest was recovered from a soluble fraction in the cell mass, and it was then roughly purified using a Ni2+ affinity column HisTrap HP (manufactured by GE Healthcare). During this purification, a 50 mM Tris-HCl, 200 mM NaCl (pH 8.0) buffer was used as a mobile phase, a stepwise elution was carried out using a 50 mM Tris-HCl, 200 mM NaCl, 500 mM imidazole (pH 8.0) buffer (FIG. 5). An eluted fraction of protein of interest was recovered, and it was then dialyzed against a 50 mM Tris-HCl, 200 mM NaCl (pH 8.0) buffer. Thereafter, final purification was carried out by size exclusion chromatography. HiLoad 26/60 Superdex 200 (GE Healthcare) was used as a column, and a 50 mM Tris-HCl, 200 mM NaCl (pH 8.0) buffer was used as a mobile phase. The final purification product was confirmed by SDS-PAGE. The results of the final purification performed by size exclusion chromatography and SDS-PAGE are shown in FIG. 6.

Example 8

Evaluation of Activity of B5209B Mouse-scFv-mcSA414

(1) Binding Ability of B5209B Mouse-scFv-mcSA414 to ROBO1

Figure 7:
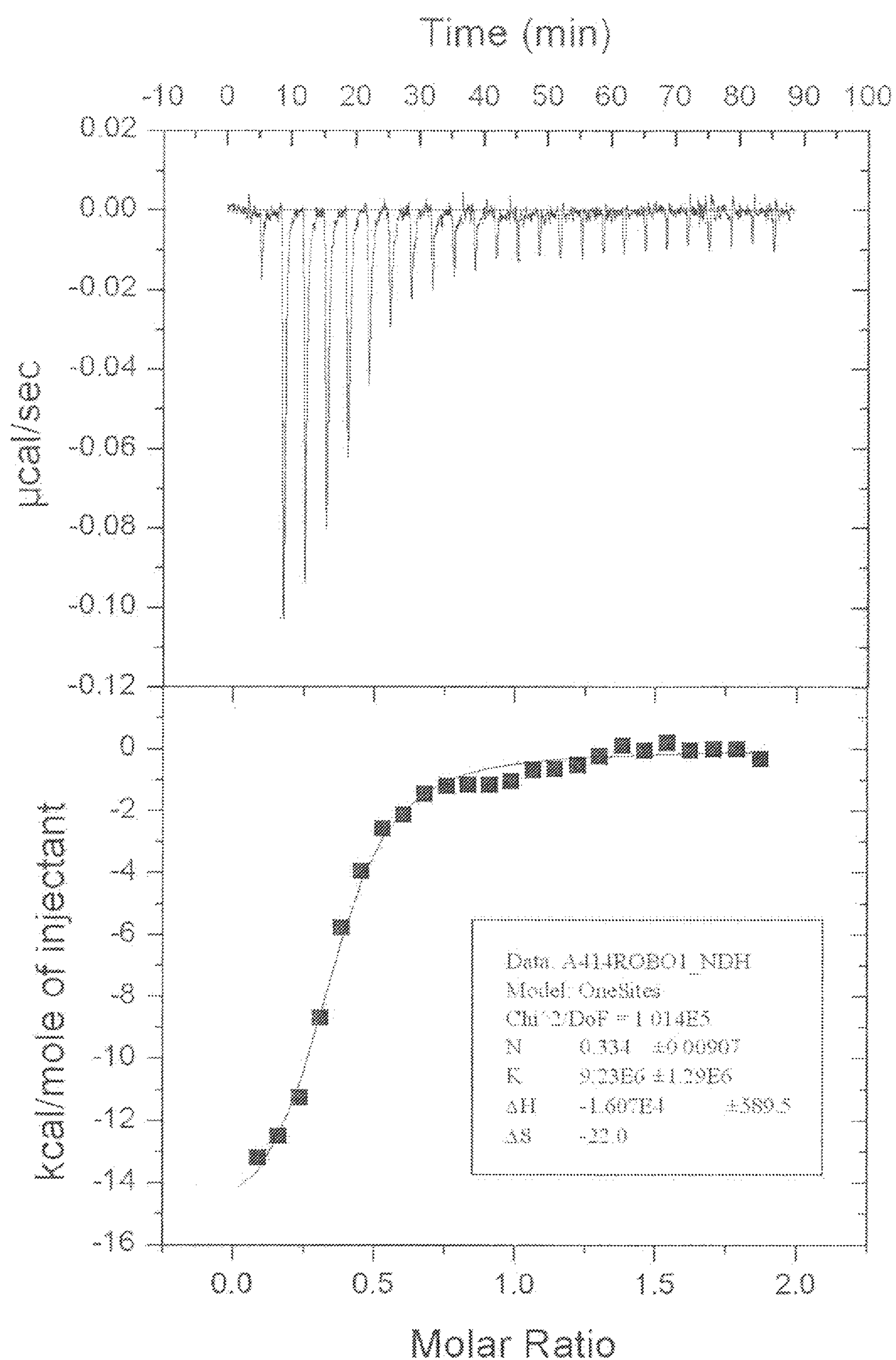
FIG. 7 shows the results of Isothermal Titration calorimetry (ITC) performed on B5209B scFv-mcSA414 and ROBO1.

By Isothermal Titration calorimetry (ITC), the interaction of B5209B mouse-scFv-mcSA414 and ROBO1 was subjected to thermohydrodynamic analysis. FIG. 7 shows the measurement results obtained by adding a constant amount of ROBO1 dropwise to B5209B mouse-scFv-mcSA414 (3.7 μM) at 25° C., using PBS as a solvent.

The calculated dissociation constant was $3.3\times10^{-8}$ (1/M), and the amount of enthalpy change (ΔH) was −16.1 kJ/mol, or the amount of entropy change (ΔS) was −22 J/mol·K. If compared with scFV, no significant change was found in ΔH. On the other hand, the ΔS value was decreased to approximately 1/40, and a reduction of approximately one order of magnitude was found in terms of affinity. Moreover, with regard to binding ratio, it was suggested that 2 molecules of ROBO 1 would bind to a tetramer of B5209B mouse-scFv-mcSA414. Thus, it is likely that only one of the two adjacent antigen-binding sites of the tetramer could recognize ROBOT due to steric hindrance.

(2) Evaluation of Binding Ability of Mouse-scFv-mcSA414 to Biotin

Figure 8:
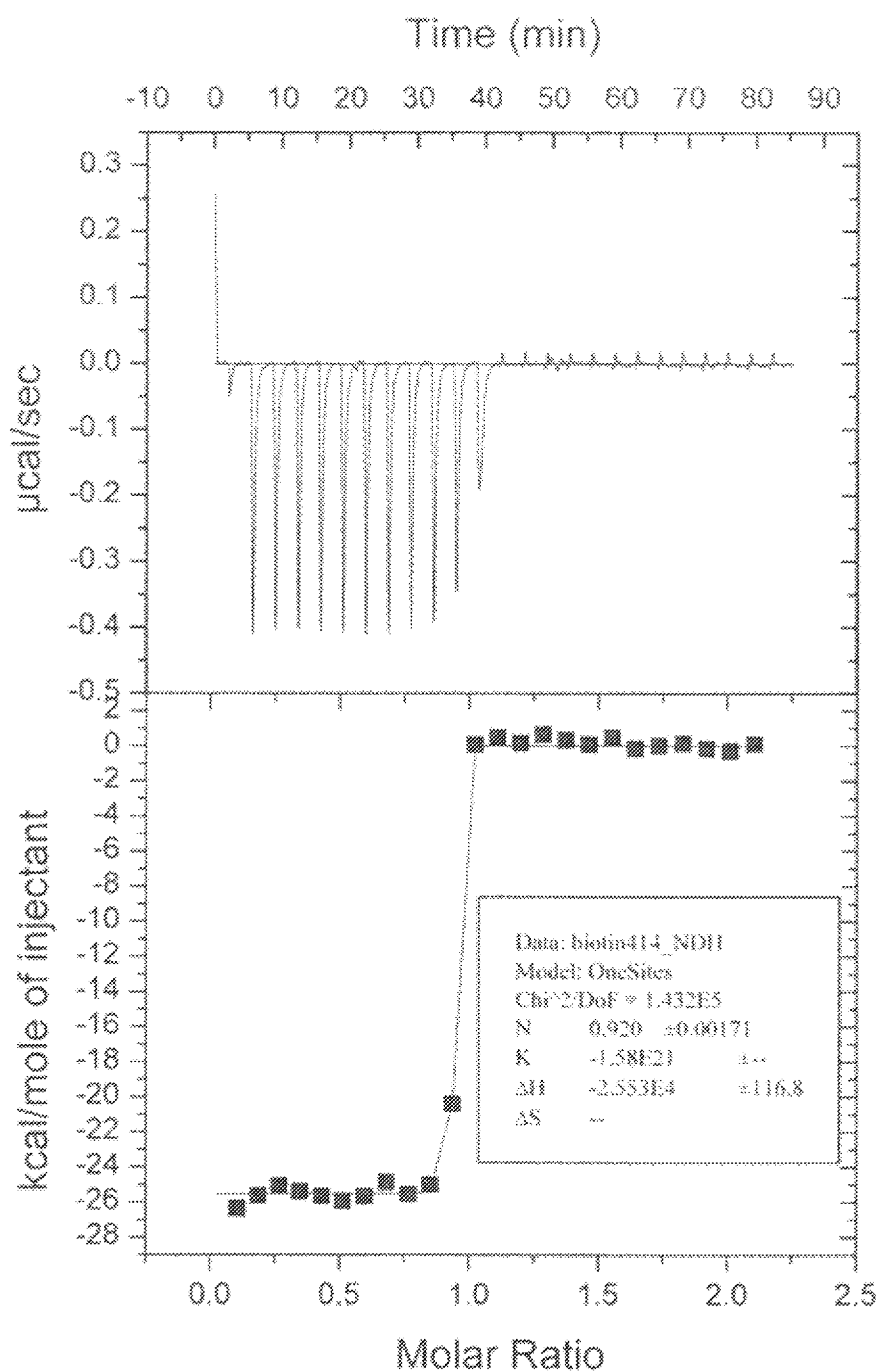
FIG. 8 shows the results of Isothermal Titration calorimetry (ITC) performed on B5209B scFv-mcSA414 and Biotin.

By Isothermal Titration calorimetry (ITC), the binding ability of B5209B mouse-scFv-mcSA414 to biotin was evaluated. FIG. 8 shows the measurement results obtained by adding a constant amount of biotin (90 μM) dropwise to B5209B mouse-scFv-SA (9 μM) at 25° C., using PBS as a solvent.

The calculated dissociation constant was $5.6\times10^{-8}$ (1/M), and the amount of enthalpy change (ΔH) was −25.5 kJ/mol, or the amount of entropy change (ΔS) was less than the detection limit.

(3) Evaluation of Thermal Stability of Mouse-scFv-mcSA414

Figure 9:
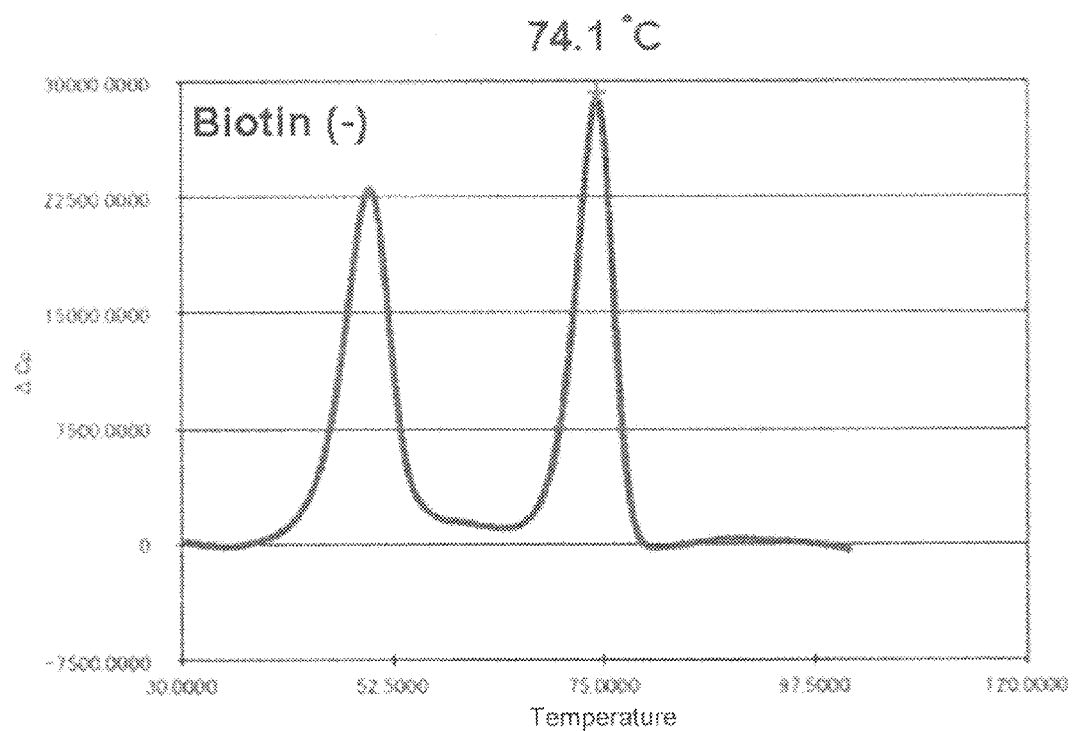
FIG. 9 shows the results of Differential Scanning calorimetry (DSC) performed on B5209B scFv-mcSA414.
Figure 9:
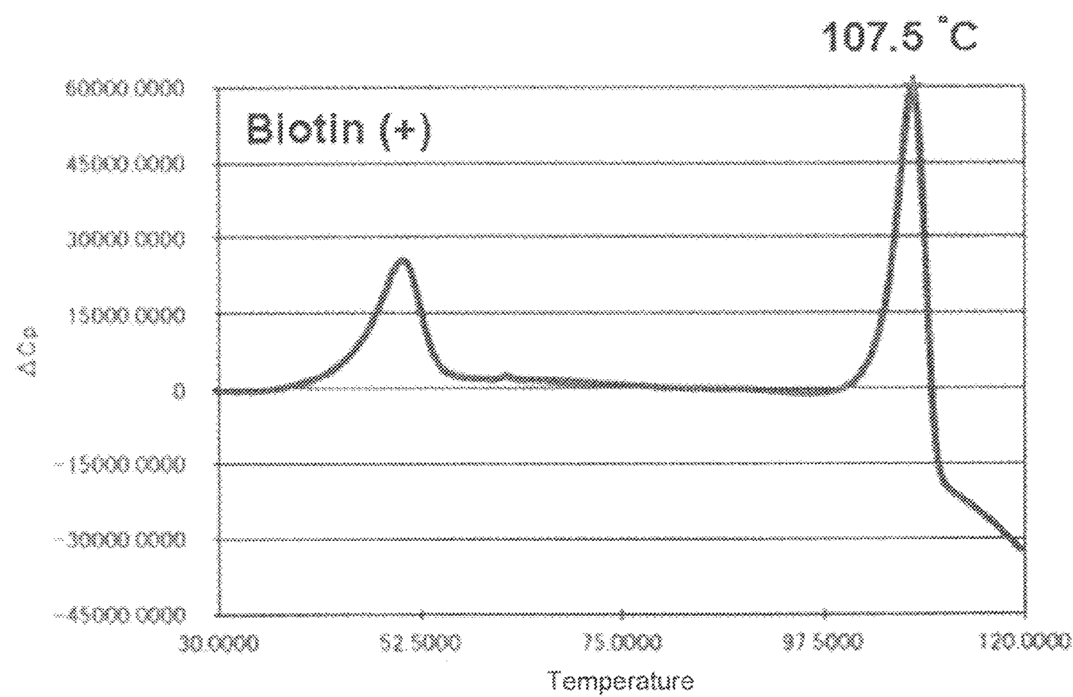

By Differential Scanning calorimetry (DSC), the thermal stability of B5209B mouse-scFv-mcSA414 was evaluated. The obtained results are shown in FIG. 9. PBS was used as a solvent. The thermal stability of B5209B mouse-scFv was found to be around 50° C. Accordingly, the temperature necessary for denaturation of the scFV domain of B5209B mouse-scFv-SA is assumed to be Tm 51.4° C., and the temperature necessary for the complete denaturation of a single molecule thereof is assumed to be Tm 108° C. Moreover, since the temperature for dissociation of a streptavidin domain tetramer was not detected, it is assumed that the streptavidin was completely denatured without the dissociation of a tetramer.

The invention claimed is:

1. A mutant streptavidin, which comprises an amino acid sequence in which (a) the arginine residue at position 72 is substituted with another amino acid residue, and (b) any one or more of the tyrosine residue at position 10, the tyrosine residue at position 71, the glutamic acid residue at position 89, the arginine residue at position 91, and the glutamic acid residue at position 104 are substituted with other amino acid residues, with respect to the amino acid sequence of a core streptavidin as shown in SEQ ID NO: 2, and which has decreased immunogenicity as compared with that of a wild-type streptavidin.

2. The mutant streptavidin according to claim 1, which comprises an amino acid sequence in which (a) the tyrosine residue at position 71 and the arginine residue at position 72 are substituted with other amino acid residues, and (b) any one or more of the tyrosine residue at position 10, the glutamic acid residue at position 89, the arginine residue at position 91, and the glutamic acid residue at position 104 are substituted with other amino acid residues, with respect to the amino acid sequence of a core streptavidin as shown in SEQ ID NO: 2.

3. The mutant streptavidin according to claim 1, which has any one or more mutations as described below with respect to the amino acid sequence of a core streptavidin as shown in SEQ ID NO: 2:

(1) a mutation in which the tyrosine residue at position 10 is substituted with serine or threonine;

(2) a mutation in which the tyrosine residue at position 71 is substituted with alanine or serine;

(3) a mutation in which the arginine residue at position 72 is substituted with lysine;

(4) a mutation in which the glutamic acid residue at position 89 is substituted with aspartic acid;

(5) a mutation in which the arginine residue at position 91 is substituted with lysine; and (6) a mutation in which the glutamic acid residue at position 104 is substituted with glutamine or asparagine.

4. A mutant streptavidin, which comprises an amino acid sequence having the mutations as described below with respect to the amino acid sequence of a core streptavidin as shown in SEQ ID NO: 2, and which has decreased immunogenicity as compared with that of a wild-type streptavidin:

(2) a mutation in which the tyrosine residue at position 71 is substituted with alanine or serine;

(3) a mutation in which the arginine residue at position 72 is substituted with lysine;

(4) a mutation in which the glutamic acid residue at position 89 is substituted with aspartic acid; and (6) a mutation in which the glutamic acid residue at position 104 is substituted with glutamine or asparagine.

5. The mutant streptavidin according to claim 4, which further comprises the following mutations:

(1) a mutation in which the tyrosine residue at position 10 is substituted with serine or threonine; and (5) a mutation in which the arginine residue at position 91 is substituted with lysine.

6. A mutant streptavidin, which comprises an amino acid sequence having all of the following mutations with respect to the amino acid sequence of a core streptavidin as shown in SEQ ID NO: 2:

(1) a mutation in which the tyrosine residue at position 10 is substituted with serine;

(2) a mutation in which the tyrosine residue at position 71 is substituted with serine;

(3) a mutation in which the arginine residue at position 72 is substituted with lysine;

(4) a mutation in which the glutamic acid residue at position 89 is substituted with aspartic acid;

(5) a mutation in which the arginine residue at position 91 is substituted with lysine; and (6) a mutation in which the glutamic acid residue at position 104 is substituted with glutamine or asparagine.

7. DNA which encodes the mutant streptavidin according to claim 1.

8. A conjugate of mutant streptavidin and antibody, which is obtained by allowing an antibody to bind to the mutant streptavidin according to claim 1.

9. A therapeutic or diagnostic agent which comprises the conjugate of mutant streptavidin and antibody according to claim 8.

10. A therapeutic or diagnostic kit, which comprises: (a) the conjugate of mutant streptavidin and antibody according to claim 8; and (b) a diagnostic or therapeutic agent labeled with biotin having an affinity for streptavidin or a derivative thereof.

* * * * *

SEQUENCE LISTING

```
<160> NUMBER OF SEQ ID NOS: 16

<210> SEQ ID NO 1
<211> LENGTH: 381
<212> TYPE: DNA
<213> ORGANISM: Streptomyces avidinii
<220> FEATURE:
<221> NAME/KEY: CDS
<222> LOCATION: (1)..(381)

<400> SEQUENCE: 1

gcc gaa gct ggt atc act ggc acc tgg tat aac caa ctg ggg tcg act        48
Ala Glu Ala Gly Ile Thr Gly Thr Trp Tyr Asn Gln Leu Gly Ser Thr
1               5                   10                  15
```

```
ttc att gtg acc gct ggt gcg gac gga gct ctg act ggc acc tac gaa       96
Phe Ile Val Thr Ala Gly Ala Asp Gly Ala Leu Thr Gly Thr Tyr Glu
            20                  25                  30

tct gcg gtt ggt aac gca gaa tcc cgc tac gta ctg act ggc cgt tat      144
Ser Ala Val Gly Asn Ala Glu Ser Arg Tyr Val Leu Thr Gly Arg Tyr
        35                  40                  45

gac tct gca cct gcc acc gat ggc tct ggt acc gct ctg ggc tgg act      192
Asp Ser Ala Pro Ala Thr Asp Gly Ser Gly Thr Ala Leu Gly Trp Thr
    50                  55                  60

gtg gct tgg aaa aac aac tat cgt aat gcg cac agc gcc act acg tgg      240
Val Ala Trp Lys Asn Asn Tyr Arg Asn Ala His Ser Ala Thr Thr Trp
65                  70                  75                  80

tct ggc caa tac gtt ggc ggt gct gag gct cgt atc aac act cag tgg      288
Ser Gly Gln Tyr Val Gly Gly Ala Glu Ala Arg Ile Asn Thr Gln Trp
                85                  90                  95

ctg tta aca tcc ggc act acc gaa gcg aat gca tgg aaa tcg aca cta      336
Leu Leu Thr Ser Gly Thr Thr Glu Ala Asn Ala Trp Lys Ser Thr Leu
            100                 105                 110

gta ggt cat gac acc ttt acc aaa gtt aag cct tct gct gct agc          381
Val Gly His Asp Thr Phe Thr Lys Val Lys Pro Ser Ala Ala Ser
        115                 120                 125


<210> SEQ ID NO 2
<211> LENGTH: 127
<212> TYPE: PRT
<213> ORGANISM: Streptomyces avidinii

<400> SEQUENCE: 2

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125


<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

gctcttcaaa gctttggccg aagctggtat cactg                                35


<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
```

primer

<400> SEQUENCE: 4
ctcgaggaat tcttagctag cagcagaagg cttaac 36

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
cactggcacc tggtcgaacc aactggggtc 30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
cactggcacc tggactaacc aactggggtc 30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
cgttggcggt gctgatgctc gtatcaacac 30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ggtgctgatg ctaagatcaa cactcagtgg 30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ggaaaaacaa cgcccgtaat gcgcacagcg 30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 10

ggaaaaacaa ctcgcgtaat gcgcacagcg                                    30


<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

gaaaaacaac tataagaatg cgcacagcg                                     29


<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

catccggcac taccaatgcg aatgcatgg                                     29


<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

catccggcac tacccaagcg aatgcatgg                                     29


<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

ccaagcttag gggccagtgg atagactg                                      28


<210> SEQ ID NO 15
<211> LENGTH: 1191
<212> TYPE: DNA
<213> ORGANISM: Mus sp.
<220> FEATURE:
<221> NAME/KEY: CDS
<222> LOCATION: (1)..(1188)

<400> SEQUENCE: 15

atg gcc gag gtg caa ttg gtg gag tct ggg gga ggc gta gtg cag cct       48
Met Ala Glu Val Gln Leu Val Glu Ser Gly Gly Gly Val Val Gln Pro
1               5                   10                  15

gga ggg tcc ctg aaa ctc tcc tgt gca gcc tct gga ttc act ttc agt       96
Gly Gly Ser Leu Lys Leu Ser Cys Ala Ala Ser Gly Phe Thr Phe Ser
            20                  25                  30

acc tat gac atg tct tgg gtt cgc cag act cca gac aag agg ctg gag      144
Thr Tyr Asp Met Ser Trp Val Arg Gln Thr Pro Asp Lys Arg Leu Glu
        35                  40                  45

ttg gtc gca acc att aat agt aat ggt ggt agt acc tat tat cca gac      192
```

-continued

```
Leu Val Ala Thr Ile Asn Ser Asn Gly Gly Ser Thr Tyr Tyr Pro Asp
    50                  55                  60

agt gtg aag ggc cga ttc acc agt tcc aga gac aat gcc aag aac atc      240
Ser Val Lys Gly Arg Phe Thr Ser Ser Arg Asp Asn Ala Lys Asn Ile
65                  70                  75                  80

ctg tac ctg caa atg agc agt ctg aag tct gag gac aca gcc atg tat      288
Leu Tyr Leu Gln Met Ser Ser Leu Lys Ser Glu Asp Thr Ala Met Tyr
                85                  90                  95

tac tgt gca aga gag gca tta cta cgg ccc cct tac tat gct ttg gac      336
Tyr Cys Ala Arg Glu Ala Leu Leu Arg Pro Pro Tyr Tyr Ala Leu Asp
            100                 105                 110

tac tgg ggt cag gga acc tca gtc acc gtc tcc tcg gcc ggc ggg ggc      384
Tyr Trp Gly Gln Gly Thr Ser Val Thr Val Ser Ser Ala Gly Gly Gly
        115                 120                 125

ggt agc ggc ggt ggc ggg tcg ggc ggt ggc gga tcg gat atc ctc gat      432
Gly Ser Gly Gly Gly Gly Ser Gly Gly Gly Gly Ser Asp Ile Leu Asp
    130                 135                 140

att cag atg acc cag tct cca gct tca ctg tct gca tct gtg gga gaa      480
Ile Gln Met Thr Gln Ser Pro Ala Ser Leu Ser Ala Ser Val Gly Glu
145                 150                 155                 160

act gtc acc atc aca tgt gga gca agt gag aat att tac ggt gct tta      528
Thr Val Thr Ile Thr Cys Gly Ala Ser Glu Asn Ile Tyr Gly Ala Leu
                165                 170                 175

act tgg tat cag cgg aaa cag gga aaa tct cct cag ctc ctg atc tat      576
Thr Trp Tyr Gln Arg Lys Gln Gly Lys Ser Pro Gln Leu Leu Ile Tyr
            180                 185                 190

ggt gca atc aat ttg gca gat gac aag tca tcg agg ttc agt ggc agt      624
Gly Ala Ile Asn Leu Ala Asp Asp Lys Ser Ser Arg Phe Ser Gly Ser
        195                 200                 205

gga tct ggt aga cag tat tct ctc aag atc agt agc ctg cat cct gac      672
Gly Ser Gly Arg Gln Tyr Ser Leu Lys Ile Ser Ser Leu His Pro Asp
    210                 215                 220

gat gtt gca acg tat tac tgt caa aat gtg tta agt act cca ttc acg      720
Asp Val Ala Thr Tyr Tyr Cys Gln Asn Val Leu Ser Thr Pro Phe Thr
225                 230                 235                 240

ttc ggc tcg ggg aca aag ttg gaa ata aaa gcc gcg ggt tct tct ggt      768
Phe Gly Ser Gly Thr Lys Leu Glu Ile Lys Ala Ala Gly Ser Ser Gly
                245                 250                 255

tct ggt tct gcg gcg gaa gct ggt atc act ggc acc tgg tcg aac caa      816
Ser Gly Ser Ala Ala Glu Ala Gly Ile Thr Gly Thr Trp Ser Asn Gln
            260                 265                 270

ctg ggg tcg act ttc att gtg acc gct ggt gcg gac gga gct ctg act      864
Leu Gly Ser Thr Phe Ile Val Thr Ala Gly Ala Asp Gly Ala Leu Thr
        275                 280                 285

ggc acc tac gaa tct gcg gtt ggt aac gca gaa tcc cgc tac gta ctg      912
Gly Thr Tyr Glu Ser Ala Val Gly Asn Ala Glu Ser Arg Tyr Val Leu
    290                 295                 300

act ggc cgt tat gac tct gca cct gcc acc gat ggc tct ggt acc gct      960
Thr Gly Arg Tyr Asp Ser Ala Pro Ala Thr Asp Gly Ser Gly Thr Ala
305                 310                 315                 320

ctg ggc tgg act gtg gct tgg aaa aac aac tcc aag aat gcg cac agc     1008
Leu Gly Trp Thr Val Ala Trp Lys Asn Asn Ser Lys Asn Ala His Ser
                325                 330                 335

gcc act acg tgg tct ggc caa tac gtt ggc ggt gct gat gct aag atc     1056
Ala Thr Thr Trp Ser Gly Gln Tyr Val Gly Gly Ala Asp Ala Lys Ile
            340                 345                 350

aac act cag tgg ctg tta aca tcc ggc act acc cag gcg aat gca tgg     1104
Asn Thr Gln Trp Leu Leu Thr Ser Gly Thr Thr Gln Ala Asn Ala Trp
        355                 360                 365

aaa tcg aca cta gta ggt cat gac acc ttt acc aaa gtt aag cct tct     1152
```

```
Lys Ser Thr Leu Val Gly His Asp Thr Phe Thr Lys Val Lys Pro Ser
    370                 375                 380

gct gct agc ggg gcc cgt cac cat cat cac cac cat taa                 1191
Ala Ala Ser Gly Ala Arg His His His His His His
385                 390                 395


<210> SEQ ID NO 16
<211> LENGTH: 396
<212> TYPE: PRT
<213> ORGANISM: Mus sp.

<400> SEQUENCE: 16

Met Ala Glu Val Gln Leu Val Glu Ser Gly Gly Gly Val Val Gln Pro
1               5                   10                  15

Gly Gly Ser Leu Lys Leu Ser Cys Ala Ala Ser Gly Phe Thr Phe Ser
            20                  25                  30

Thr Tyr Asp Met Ser Trp Val Arg Gln Thr Pro Asp Lys Arg Leu Glu
        35                  40                  45

Leu Val Ala Thr Ile Asn Ser Asn Gly Gly Ser Thr Tyr Tyr Pro Asp
    50                  55                  60

Ser Val Lys Gly Arg Phe Thr Ser Ser Arg Asp Asn Ala Lys Asn Ile
65                  70                  75                  80

Leu Tyr Leu Gln Met Ser Ser Leu Lys Ser Glu Asp Thr Ala Met Tyr
                85                  90                  95

Tyr Cys Ala Arg Glu Ala Leu Leu Arg Pro Pro Tyr Tyr Ala Leu Asp
            100                 105                 110

Tyr Trp Gly Gln Gly Thr Ser Val Thr Val Ser Ser Ala Gly Gly Gly
        115                 120                 125

Gly Ser Gly Gly Gly Gly Ser Gly Gly Gly Gly Ser Asp Ile Leu Asp
    130                 135                 140

Ile Gln Met Thr Gln Ser Pro Ala Ser Leu Ser Ala Ser Val Gly Glu
145                 150                 155                 160

Thr Val Thr Ile Thr Cys Gly Ala Ser Glu Asn Ile Tyr Gly Ala Leu
                165                 170                 175

Thr Trp Tyr Gln Arg Lys Gln Gly Lys Ser Pro Gln Leu Leu Ile Tyr
            180                 185                 190

Gly Ala Ile Asn Leu Ala Asp Asp Lys Ser Ser Arg Phe Ser Gly Ser
        195                 200                 205

Gly Ser Gly Arg Gln Tyr Ser Leu Lys Ile Ser Ser Leu His Pro Asp
    210                 215                 220

Asp Val Ala Thr Tyr Tyr Cys Gln Asn Val Leu Ser Thr Pro Phe Thr
225                 230                 235                 240

Phe Gly Ser Gly Thr Lys Leu Glu Ile Lys Ala Ala Gly Ser Ser Gly
                245                 250                 255

Ser Gly Ser Ala Ala Glu Ala Gly Ile Thr Gly Thr Trp Ser Asn Gln
            260                 265                 270

Leu Gly Ser Thr Phe Ile Val Thr Ala Gly Ala Asp Gly Ala Leu Thr
        275                 280                 285

Gly Thr Tyr Glu Ser Ala Val Gly Asn Ala Glu Ser Arg Tyr Val Leu
    290                 295                 300

Thr Gly Arg Tyr Asp Ser Ala Pro Ala Thr Asp Gly Ser Gly Thr Ala
305                 310                 315                 320

Leu Gly Trp Thr Val Ala Trp Lys Asn Asn Ser Lys Asn Ala His Ser
                325                 330                 335

Ala Thr Thr Trp Ser Gly Gln Tyr Val Gly Gly Ala Asp Ala Lys Ile
            340                 345                 350
```

-continued

```
Asn Thr Gln Trp Leu Leu Thr Ser Gly Thr Thr Gln Ala Asn Ala Trp
        355                 360                 365

Lys Ser Thr Leu Val Gly His Asp Thr Phe Thr Lys Val Lys Pro Ser
    370                 375                 380

Ala Ala Ser Gly Ala Arg His His His His His His
385                 390                 395
```